(12) United States Patent
Martin et al.

(10) Patent No.: US 7,186,235 B2
(45) Date of Patent: *Mar. 6, 2007

(54) DEVICE FOR MANIPULATING A NEEDLE OR ABRADER ARRAY AND METHOD OF USE

(75) Inventors: Frank E. Martin, Durham, SC (US); John D. Evans, Los Angeles, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 699 days.

This patent is subject to a terminal disclaimer.

(21) Appl. No.: 10/163,383

(22) Filed: Jun. 7, 2002

(65) Prior Publication Data

US 2002/0188245 A1    Dec. 12, 2002

Related U.S. Application Data (60) Provisional application No. 60/297,101, filed on Jun. 8, 2001.

(51) Int. Cl.
*A61B 17/20* (2006.01)

(52) U.S. Cl. .......... 604/22; 604/185; 604/212; 604/500; 604/264

(58) Field of Classification Search ........ 604/290, 604/289, 181, 185, 212, 218, 20, 272–274, 604/22, 46, 47, 500, 501, 511, 512, 264, 93.01
See application file for complete search history.

(56) References Cited

U.S. PATENT DOCUMENTS

| | | | |
|---|---|---|---|
| 3,735,760 A | 5/1973 | Vreeland, Jr. | |
| 3,964,482 A | 6/1976 | Gerstel et al. | |
| 5,003,987 A | 4/1991 | Grinwald | |
| 5,273,528 A | 12/1993 | Skeen et al. | |
| 5,501,784 A | 3/1996 | Lessmollmann et al. | |
| 5,658,515 A | 8/1997 | Lee et al. | |
| 5,660,680 A | 8/1997 | Keller | |
| 5,679,647 A | 10/1997 | Carson et al. | |
| 5,848,991 A | 12/1998 | Gross et al. | |
| 5,855,801 A | 1/1999 | Lin et al. | |
| 5,879,326 A | 3/1999 | Godshall et al. | |
| 5,885,211 A | 3/1999 | Eppstein et al. | |
| 5,910,306 A | 6/1999 | Alving et al. | |
| 5,919,364 A | 7/1999 | Lebouitz et al. | |
| 5,928,207 A | 7/1999 | Pisano et al. | |
| 5,931,794 A | 8/1999 | Pitesky | |
| 5,958,589 A | 9/1999 | Glenn et al. | |
| 5,970,998 A | 10/1999 | Talbot et al. | |
| 5,980,898 A | 11/1999 | Glenn et al. | |

(Continued)

FOREIGN PATENT DOCUMENTS

EP    0 381 410 A1    8/1990

(Continued)

*Primary Examiner*—Cris L. Rodriguez
(74) *Attorney, Agent, or Firm*—Robert E. West (57) ABSTRACT

The present invention relates to an apparatus and method for intradermally administering a pharmaceutical composition or other substance into and through the skin of a mammalian body in a manner that avoids or eliminates excess pain and discomfort normally caused as a result of the microabraders or microneedles entering the epithelial layers beneath the stratum corneum. In a preferred embodiment, the apparatus is a microdevice with an array of microabraders or microneedles with a manipulating member.

27 Claims, 8 Drawing Sheets

U.S. PATENT DOCUMENTS

| | | |
|---|---|---|
| 6,015,599 A | 1/2000 | Keller et al. |
| 6,065,864 A | 5/2000 | Evans et al. |
| 6,106,751 A | 8/2000 | Talbot et al. |
| 6,132,755 A | 10/2000 | Eicher et al. |
| 6,173,202 B1 | 1/2001 | Eppstein |
| 6,183,434 B1 | 2/2001 | Eppstein |
| 6,187,210 B1 | 2/2001 | Lebouitz et al. |
| 6,190,367 B1 | 2/2001 | Hall |
| 6,256,533 B1 | 7/2001 | Yuzhakov et al. |
| 6,312,612 B1 | 11/2001 | Sherman et al. |
| 6,334,856 B1 | 1/2002 | Allen et al. |
| 6,440,096 B1 * | 8/2002 | Lastovich et al. ............ 604/27 |
| 6,558,361 B1 * | 5/2003 | Yeshurun .................... 604/272 |
| 6,607,513 B1 * | 8/2003 | Down et al. ................. 604/239 |
| 6,611,707 B1 * | 8/2003 | Prausnitz et al. ............. 604/21 |
| 6,656,147 B1 * | 12/2003 | Gertsek et al. ............... 604/28 |
| 6,659,982 B2 * | 12/2003 | Douglas et al. ............. 604/173 |
| 6,743,211 B1 * | 6/2004 | Prausnitz et al. ........... 604/239 |

FOREIGN PATENT DOCUMENTS

| | | |
|---|---|---|
| EP | 0 509 122 B1 | 10/1996 |
| EP | 1 092 444 A1 | 4/2001 |
| WO | WO 96/07369 | 3/1996 |
| WO | WO 97/48440 | 12/1997 |
| WO | WO 97/48442 | 12/1997 |
| WO | WO 99/00155 | 1/1999 |
| WO | WO 99/43350 | 9/1999 |
| WO | WO 00/74763 A2 | 12/2000 |
| WO | WO 01/93946 A1 | 12/2001 |

* cited by examiner

DEVICE FOR MANIPULATING A NEEDLE OR ABRADER ARRAY AND METHOD OF USE

This application claims priority to previously filed provisional application Ser. No. 60/297,101 filed on Jun. 8, 2001.

FIELD OF THE INVENTION

The invention relates to a new and useful method and apparatus for delivering a substance to a patient. The apparatus of the present invention includes a microabrader or microneedle device which includes a reservoir containing a pharmaceutically active compound for administration into a mammalian body through abrasions or perforations in the stratum corneum layer of the epidermis.

BACKGROUND OF THE INVENTION

Transdermal, or percutaneous, administration of pharmaceutical compounds is a known method of delivering drug compounds, or other agents, through the skin and into the human, or mammalian, circulatory system. The layer primarily responsible for inhibition of agents through the skin is the stratum corneum. The stratum corneum is a heterogeneous layer of flattened, relatively dry keratinised cells which limits the rate at which such agents can be administered therethrough, because of the chemical keratin-phospholipid complex it contains. Once a compound has penetrated the stratum corneum, which is approximately 15 microns thick, when dry, and expands to approximately 47 microns in thickness when fully hydrated, there remains no significant hindrance to penetration of the remaining epidermal layers. The remaining epithelial layers of the skin—the stratum granulosum, the stratum malpighii and the stratum germinativum—provide little, if any, resistance to the transmission of pharmaceutical compounds. Accordingly, once the stratum corneum has been penetrated, topically administered pharmaceutical agents are adsorbed through the lower epithelial layers and are able to enter into the circulatory system through the capillaries.

The prior art reports a variety of devices and methods for disrupting the stratum corneum for the purpose of delivering substances to the body. For example, breach of the stratum corneum may be achieved by puncturing as taught in U.S. Pat. No. 5,679,647 to Carson, et al. This patent teaches that narrow diameter tines, such as those found on devices used for tuberculin skin tests and allergy tests, can be coated with polynucleotides or oligonucleotides and used for delivery of such materials into the skin. The method of using such devices involves puncturing the skin with the types resulting in intracutaneous injection of the coated substance.

U.S. Pat. No. 5,003,987; U.S. Pat. No. 5,879,326; and U.S. Pat. No. 3,964,482 teach breaching the stratum corneum by abrasion.

It is, therefore, desirable to have an article of manufacture for transdermal drug delivery which can penetrate or abrade the stratum corneum using micron-sized projections, with a device for administering a pharmaceutical agent with precision and without causing undue intrusion into the lower epithelial layers, thereby minimizing patient discomfort or irritation.

SUMMARY OF THE INVENTION

A method and device for administering a substance to a mammal are provided by the present invention. The device can comprise a top or upper surface or wall, a bottom surface or wall spaced apart from said top surface or wall. The bottom surface or wall has a substantially planar outer surface from which a plurality of projecting structures extend outward. One or more side walls may join with the top and bottom walls to define in the space between them a reservoir for a substance that is to be delivered to the mammal. The device also comprises a manipulating member which is attached to at least one of the walls or surfaces of the device. The manipulating member extends outward from the surface or surfaces of attachment and is configured so as to be allow the user of the device to grip and control the device. The manipulating member may also be an extension of one or more walls or surfaces of the device and may even be molded as a single, unit body with the device. At least one passageway also extends from the reservoir to the projecting structures on the exterior of the device. The passageway or passageways may also extend through the projecting structures themselves. The device also comprises a at least one deformable member that will exert pressure on the substance contained in the reservoir and that deformable member may be one of the device walls or surface, the manipulating member or combinations thereof. In an alternate embodiment it is preferable that the device also comprise a way of retaining the substance to be delivered within the reservoir until sufficient pressure is exerted upon the substance to dispense it from the reservoir.

These and other aspects of the invention will become apparent to those skilled in the art in view of the following detailed description of the invention and the annexed drawings.

BRIEF DESCRIPTION OF THE DRAWINGS

The following is a brief description of the drawings in which.

DETAILED DESCRIPTION OF THE INVENTION

The present invention is directed to a method and device for delivering a substance through the skin of a patient. The following description of the invention primarily relates to drug delivery devices.

The present invention is directed to a method and apparatus for delivering a substance through the skin of a patient. One aspect of the invention is directed to a device for manipulating a microneedle or microabrading device employing micron-sized projections, to penetrate or abrade the stratum corneum. A microdevice according to the present invention is a device which has a top wall and a bottom wall separated and joined by side walls, or walls which are continuous with the top wall to form a reservoir therebetween, and a substantially planar surface on the bottom wall with a plurality of projecting structures which can include either micron-sized penetrating members such as microneedles or micron-sized abrading members.

The projecting structures can range in length and width from less than 1 micron to several hundred microns. The projecting structures can be solid or hollow. The device may also include an axial passageway or channel from the reservoir to the projecting structures for conducting a substance from the reservoir to the projecting structures where the substance can be delivered through the stratum corneum and to the lower epithelial layers of a patient's skin. The passageway or channels maybe singular or multiple and may be located in or through one or more projections or on the substantially planar surface that houses the projections. The present invention is contemplated for use with mammalian patients.

In one embodiment of the invention, the microdevice has an extension to permit the manipulation of the microdevice by the user. The extension can be a stick-like elongated manipulation member such as a handle, finger-cup, or any other configuration that allows the user to control and manipulate the microdevice. The manipulation member may also contain a fluid reservoir that is either in fluid communication with an array of microneedles or microabraders or in communication with the internal reservoir containing a substance to be administered. The manipulation member is used to position the projecting structures accurately on the patient's skin to enable the user to retain control of the device. The manipulation member enables one to control the microdevice when moving the array of microneedles or abrading structures in a manner that penetrates or scores the stratum corneum while minimizing the risk of piercing the stratum corneum and penetrating into the lower epithelial layers and causing the patient excessive discomfort or irritation.

A substance, such as a pharmaceutical agent, is stored in a reservoir, it may also be stored in the handle. By squeezing and deforming the manipulation member, the fluid in the member impinges on the reservoir and the substance within the reservoir is forced out through the passageways or channels and delivered into and through the stratum corneum without having to increase the amount of pressure against the skin. If the handle is the reservoir the substance will be directly forced out through the passageways or channels.

In another embodiment of the invention, the microdevice includes a thimble-like structure or finger-cup that is comfortably and securely fitted to a fingertip. The thimble-like element of the device has an open end for inserting a finger and the projecting structure at the opposite end. A reservoir is disposed with one side in fluid communication with the projecting structures. The opposite side, or the adjacent sides may be deformable such as by including one or more membranes formed of resilient material to allow the fingertip within the thimble-like structure to deform and dispense the substance from the reservoir, by exerting pressure against the deformable material. This allows a person to accurately place the microdevice on the patient's skin and apply the necessary force to penetrate the stratum corneum and assist the percutaneous delivery of a drug composition within the reservoir, without increasing the depth to which the microneedles or abrading projections penetrate through the epithelial layer of the skin.

The aspects of the invention are basically attained by providing a device for administering a substance to a patient. The device comprises a top wall and a handle attached to the top wall and extending outward therefrom. The handle has a dimension sufficient to grip the device. A bottom wall is spaced apart from the top wall and has a planar outer surface. A plurality of projecting structures extend outwardly from the planar surface. Side walls join the top wall and the bottom wall. The top wall, bottom wall and side walls define a reservoir for the substance to be delivered into and through the skin of a patient.

The aspects of the invention are also attained by providing a device for delivering a substance through the skin of a patient. The device comprises a top wall, a finger-cup attached to the top wall and extending outward therefrom, and a bottom wall spaced apart from the top wall and having a planar outer surface. Projecting structures extend outward from the planar surface. Side walls join the top wall and the bottom wall. The top wall, bottom wall and side walls define a reservoir for the substance to be delivered to a patient.

The aspects of the invention are further attained by providing a method of delivering a substance through the skin of a patient. A microdevice is placed in contact with the skin of a patient. The microdevice comprises a planar surface having a plurality of projecting structures extending outwardly therefrom. A top wall is spaced apart from the planar surface. Side walls join the top wall and the planar surface to define a reservoir containing a substance. A manipulating member is attached to the top wall. A sufficient force is applied to the microdevice to cause the projecting structures to penetrate the stratum corneum layer of the skin. The substance is dispensed from the reservoir to the projecting structures and the substance is delivered below the stratum corneum layer of the skin.

The present invention relates to a microdevice with a structure for gripping or holding the microdevice during use. The microdevice of the present invention enables the person using the device to accurately and conveniently position and operate the microdevice, while reducing the possibility of causing penetration of the epithelial layers of the skin below the stratum corneum. By constructing a microdevice to enable greater control over its placement and operation, the stratum corneum can be abraded or pierced without the need for the application of excess pressure to the microdevice. By reducing the amount of pressure applied to the microdevice, the microneedles or microabraders of the microdevice when appropriately sized will penetrate the epithelial layer to a depth no greater than is necessary to deliver a substance below the stratum corneum without causing unintentional abrasion or penetration of the lower epithelial layers, thereby reducing patient irritation and discomfort.

In yet other embodiments of the invention the features of the device that are useful for delivering the substance from the reservoir are configured so that only at a predetermined pressure threshold is the delivery of the substance from the reservoir accomplished. In an embodiment with a deformable manipulating member, for example, that member will only deform, not under the forces or pressures encountered during manipulation of the device but at some higher threshold. In another example, such a pressure sensitive threshold could be set by use of a substance retaining membrane or a plug in the fluid passageway that would only rupture or be displaced at a pressure threshold greater than the pressure the substance will encounter during manipulation of the device.

Figure 1:
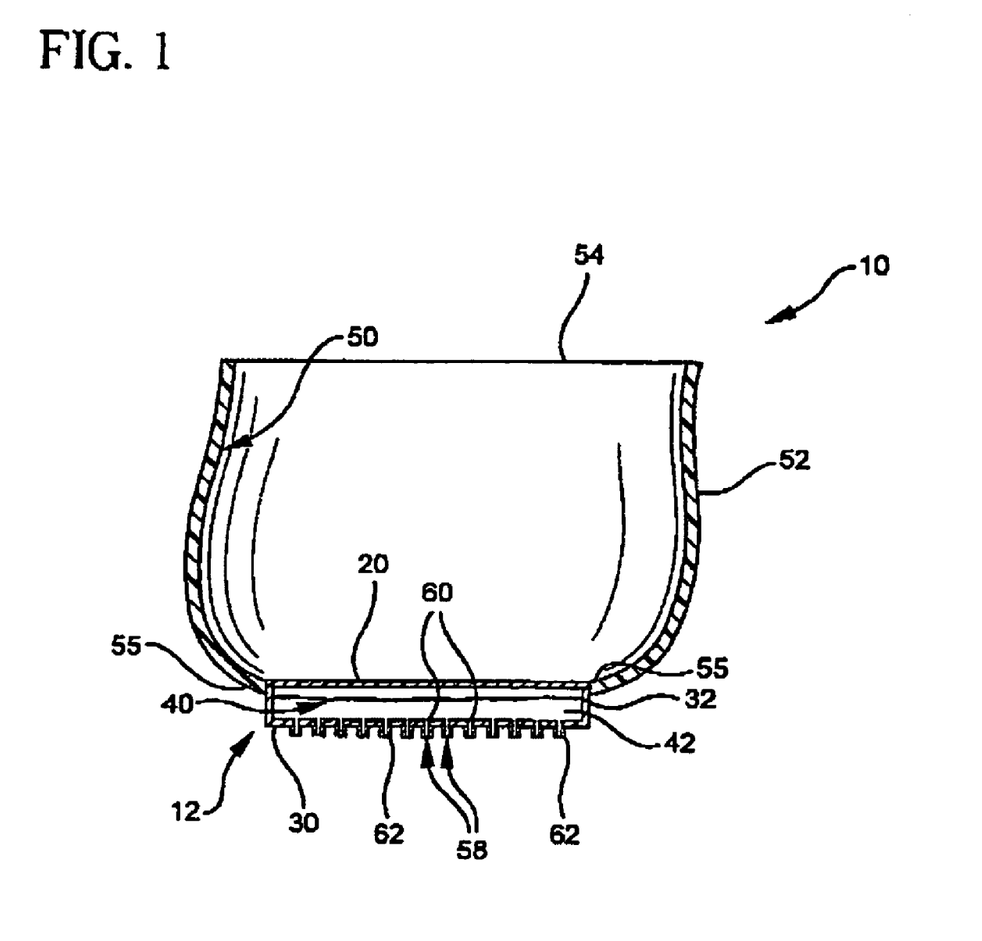
FIG. 1 is a side view in cross section of an embodiment of the present invention showing a finger-cup attached to a microdevice which includes an array of microneedles.

In accordance with the invention and with respect to the drawing figures, a first embodiment of the present invention is a microdevice 10 as shown in FIG. 1 includes a body 12 which has a top wall 20 and a bottom wall 30 spaced apart from the top wall 20 and joined by side walls 32. The interior region created by the intersection of the top wall 20, bottom wall 30 and side walls 32 defines a reservoir 40 for storing a substance 42 to be delivered to a patient. Typically, the substance is a pharmaceutical composition in a liquid or other flowable form such as gel or paste.

It is to be understood that in all of the descriptions of the figures, top and side and bottom are used for convenience and are not necessarily to be construed literally. For example, the body 12 may also be made up only one, or more, wall(s) that are a formed as a single unit body, such as for example ovoid or circular, and enclose the reservoir without distinction between top and side, or as part of another piece of the device.

Attached to top wall 20 and extending outwardly is a finger-cup 50 to receive and secure to the fingertip of a person using microdevice 10 to administer a substance to a patient. In preferred embodiments, finger-cup 50 is an elastic thimble-like member made of an elastic polymeric material. Finger-cup 50 is a tubular shaped member having a side wall 52 for encircling the finger of a user and an open top end 54. A bottom end 55 of finger cup 50 is coupled to top wall 20. In the embodiment illustrated, top wall 20 forms the bottom inner surface of finger cup 50. In an alternative embodiment, finger cup 50 can have a bottom wall that overlies top wall 20.

By securing finger-cup 50 to a finger 64, the microdevice 10 is able to be precisely maneuvered into the desired position on the skin 56 where treatment is to be administered. For greater comfort to the person administering treatment with the microdevice, the finger-cup 50 may be formed in a manner which is specific to the fingers of a left hand or right hand or be adapted to accommodate more than one finger. It is understood that fingers may include either opposing digits or thumbs or combinations of thereof.

Bottom wall 30 of the microdevice 10 has an outwardly facing planar surface having outwardly extending projections 58. The projecting structures 58 can be assembled in an array of microneedles or microabraders depending on the method desired for creating openings in the stratum corneum. The projecting structures 58 extend outwardly and generally perpendicularly from the planar surface of bottom wall 30. Fluid conducting passageways 60 are preferably included within each projecting structure 58 in the form of axial channels that extend through each projecting structure 58. The fluid conducting passageways 60 are open on each end to allow fluid communication between the reservoir 40 and tips 62 of the projecting structures 58. In one embodiment, the tips 62 of the projecting structures 58 have a length to penetrate the skin slightly beneath the stratum corneum. The fluid conducting passageways 60 permit the flow of the substance 42 from the reservoir 40 through passageways 60 of projecting structures 58 to the area immediately beneath the stratum corneum. The substance delivered in this manner is then absorbed into the capillaries through the lower epithelial layers.

In yet another embodiment, the projecting structures are solid and the passageway, or multiple passageways, opens from the interior of the reservoir to the base of the projecting structures. The form and shape of the projecting structures can be of any design and shape that will enable them to penetrate the stratum corneum is the desire manner. Such design and configurations will be apparent to those skilled in the art.

Body 12 is preferably made of a suitable plastic material, but can be any material able to perform and withstand the forces encountered and be impervious and non-reactive with any materials it may encounter. Top wall 20 is preferably flexible or deformable so as to be deflected inwardly to dispense the substance contained in reservoir 40. Bottom wall 30 is generally stiff to promote uniform penetration of projecting structures 58. In other embodiments, bottom wall 30 is flexible to conform to the surface of the skin of the patient. In yet other embodiments one or more of the side walls are deformable.

Figure 2:
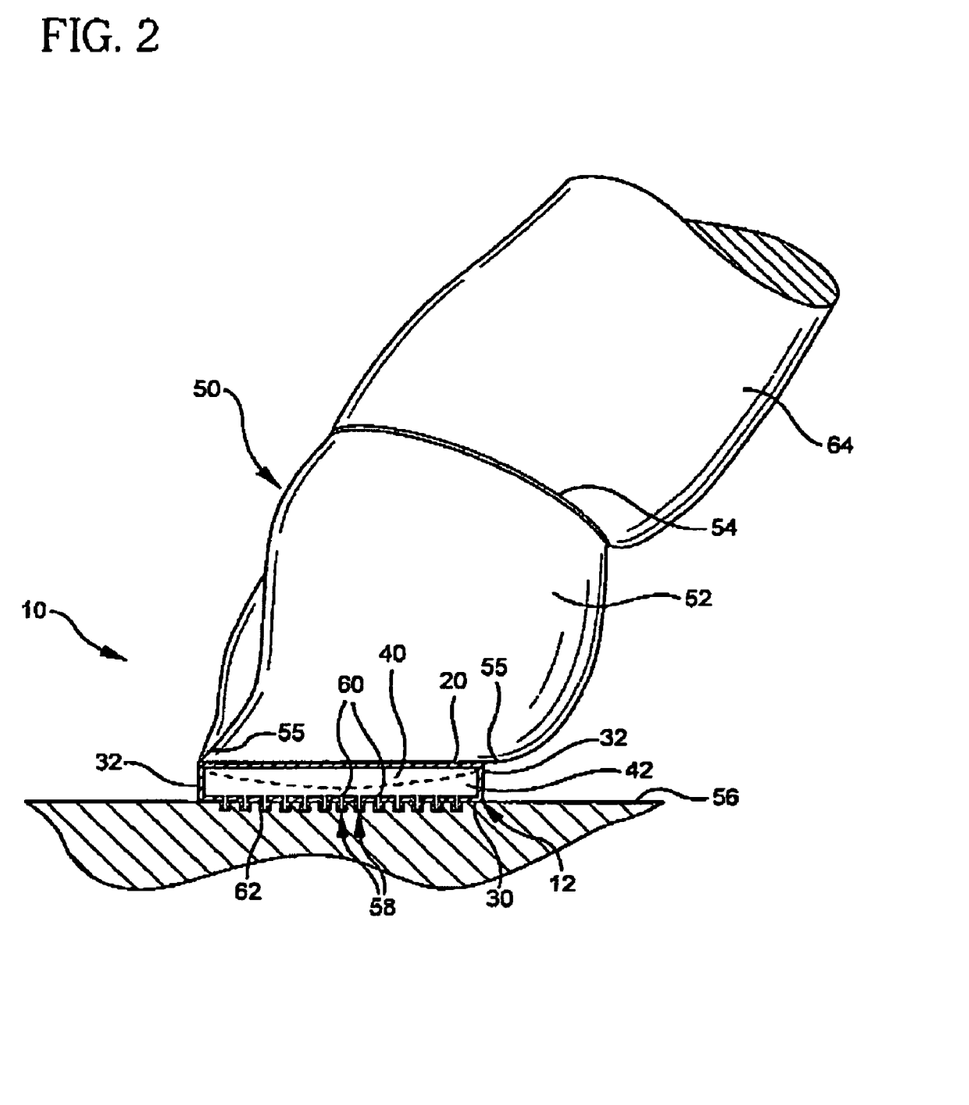
FIG. 2 is a side view in partial cross-section of the embodiment of FIG. 1 showing a human finger inserted into the finger-cup attached to the microdevice and an array of microneedles.

In FIG. 2, the tip of a finger 64 is inserted into the open top end 54 of finger-cup 50. The elasticity of the finger-cup 50 firmly secures the finger 64 within the finger-cup 50 allowing the accurate manipulation of the microdevice 10. Once the microdevice 10 has been properly positioned on the patient's skin 56, the tip of the finger 64 within the finger-cup 50 applies an additional amount of pressure against the top wall 20 of the microdevice 10. When the projecting structures 58 are microneedles as shown in FIG. 2, application of sufficient pressure against top wall 20 of microdevice 10 causes the projecting structures 58 to penetrate the stratum corneum until the bottom wall 30 of the microdevice 10 comes in contact with the surface of the patient's skin. Provided that the length of the projecting structures 58 is greater than the thickness of the stratum corneum, the tips 62 of the projecting structures 58 will pierce the stratum corneum.

As used herein, penetrating refers to entering the stratum corneum without passing completely through the stratum corneum and entering into the adjacent layers. This is not to say that that the stratum corneum can not be completely penetrated to reveal the interface of the underlying layer of the skin. Piercing, on the other hand, refers to passing through the stratum corneum completely and entering into the adjacent layers below the stratum corneum.

The downward pressure on top wall 20 by finger 64 deflects top wall 20 inwardly as shown by phantom lines in FIG. 2 to dispense the substance 42 from reservoir 40 through passageways 60 of each projecting structure 58. The substance 42 stored within the reservoir 40 is discharged through the fluid conducting passageways 60 and absorbed by the patient through the epithelial layers beneath the stratum corneum.

The length and thickness of the projecting structures 58 are selected based on the particular substance being administered and the thickness of the stratum corneum in the location where the device is to be applied. Preferably, the projecting structures 58 penetrate the stratum corneum substantially without piercing or passing through the stratum corneum. The projecting structures 58 can have a length up to about 500 microns. Suitable projecting structures 58 have a length of about 5 to 500 microns. Preferably, the projecting structures 58 have a length of about 50 to about 300 microns, and more preferably in the range of about 75 to 250 microns, with 180 to 220 microns most preferred. In preferred embodiments, the projecting structures 58 are either hollow or solid members.

The method of delivering a substance through the skin of a patient using device 10 places the projecting structures 58 against skin and applies a downward pressure. In embodiments where the projecting members 58 have a length sufficient to penetrate the skin to below the stratum corneum, the downward pressure is sufficient to penetrate the skin. In other embodiments, the device 10 is moved in a back and forth or circular pattern to abrade the skin sufficiently to enable projecting structures 58 to penetrate the skin to a desired depth. A continued downward pressure flexes top wall 20 to dispense the substance in reservoir 40 for delivery through the axial passages 60 of projecting structures 58 and into the skin.

In one embodiment, projecting structures 58 are knife-like blades or other structures, such as pyramidal or frustoconical in shape, which are preferably perpendicular to the plane of the device and abrasive to the topmost epithelial layer and able to penetrate the stratum corneum by cutting, scoring, or abrading the surface of the stratum corneum until an opening of sufficient depth has been created for fluid to pass through. Because the microdevice 10 may need to be moved in a reciprocating manner to penetrate the stratum corneum, precise handling of microdevice 10 through the use of the attached finger-cup 50 is highly desirable. Careful use of device 10 will avoid unintentional penetration, abrasion, or piercing of the epithelial layers below the stratum corneum, and avoid unnecessary patient discomfort and irritation.

Figure 3:
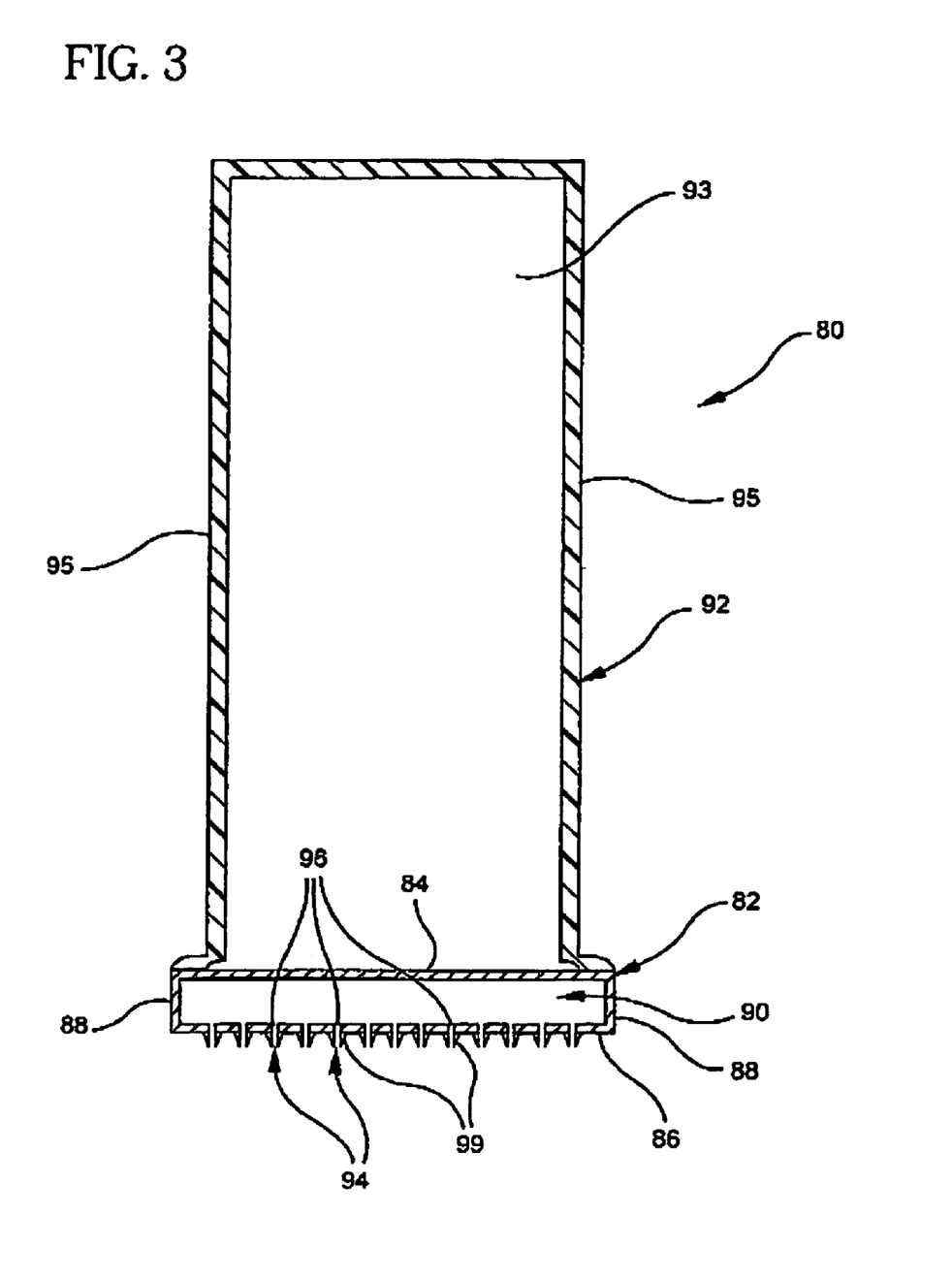
FIG. 3 is a cross-sectional side view of another embodiment of the present invention in which a handle extends outward from a flexible top wall of a reservoir wherein the microdevice includes an array of microabraders projecting outwardly from the planar surface of the bottom wall of the microdevice.
Figure 4:
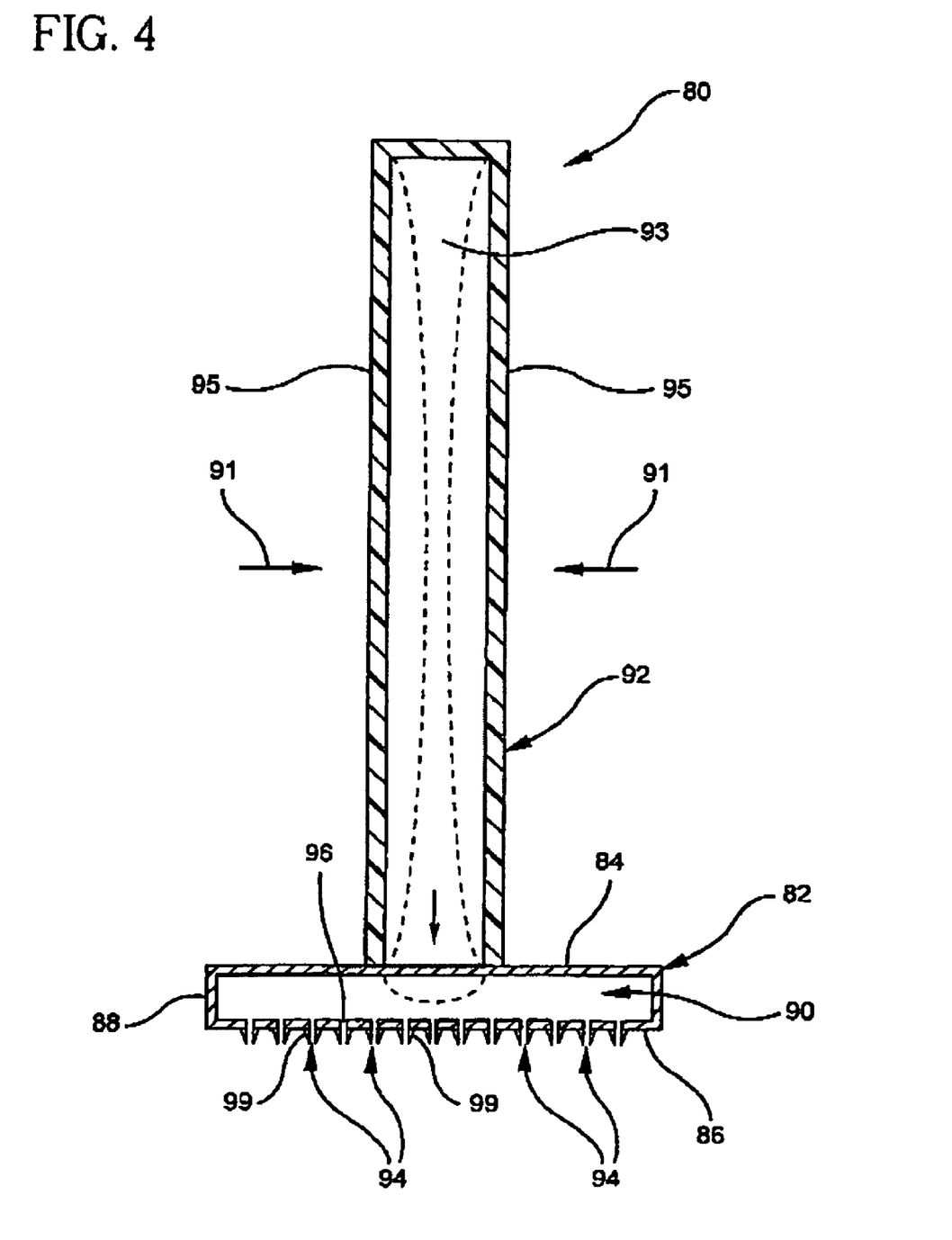
FIG. 4 is an end view in cross-section of the device of FIG. 3.

EMBODIMENT OF FIGS. 3 AND 4

FIGS. 3 and 4 show a second embodiment of a delivery device 80 of the present invention which includes a body 82 having a top wall 84, bottom wall 86 and side walls 88 defining a reservoir 90. A handle 92 is attached to top wall 84 and has a dimension to enable the user to grip and manipulate the device 80. The depicted embodiment shows handle 92 being hollow and attached to the periphery of side wall 88. In a preferred embodiment, handle 92 is made of a resilient, flexible and deformable material such as for example rubber, plastic, thin metal sheet, or combinations thereof. Handle 92 in the illustrated embodiment has a hollow cavity 93 formed by side walls 95 and a top wall 84. In one embodiment handle 92 has an open bottom end that is closed by the attachment to top wall 84. In another preferred embodiment, handle 92 is closed at both ends.

A plurality of projecting structures 94 extend from bottom wall 86 to form an array. As in the previous embodiment, projecting structures 94 have a length and width that is sufficient to penetrate the skin to a selected depth for delivering a substance into and through the skin. In this embodiment, each projecting structure 94 includes an axial passage 96 extending from reservoir 90 to ends 99 of projecting structures 94. The handle 92 is attached to top wall 84 in a manner which is air-tight to form hollow cavity 93. By squeezing the handle 92 in the direction of arrows 91, side walls 95 deflect inwardly to compress the air within handle 92 causing downward displacement of the top wall 84 as shown by the phantom lines in FIG. 4. The deflection of top wall 84 dispenses the contents of reservoir 90 through axial passages 96 of projections 94. In this manner, there is no increase in the pressure applied to the skin by the microdevice 80, thereby reducing the risk of penetration into the epithelial by the projecting structures 94. Patients treated by the present invention can expect to experience less pain and discomfort than is normally associated with the administration of pharmaceuticals by microdevices of this nature.

In practice, a person is able to administer a substance, such as a pharmaceutical composition, to a patient with device 80 by grasping the handle 92 and precisely positioning the projecting structures 94 on the skin in a target area. Once the projections 94 are properly positioned on the skin of the patient, the handle 92 is used to apply gentle pressure and to move the projecting structures 94 in a generally reciprocal manner to enable projecting structures 94 to score and abrade the stratum corneum. Once projecting structures 94 have penetrated the stratum corneum, the bottom wall 86 of the microdevice 80 is, or in the case of abrader projecting structures the projecting structures themselves are held in contact with the skin of the patient. The handle 92 is squeezed to compress fluid air contained in the handle and to produce an additional amount of pressure on top wall 84 to deflect top wall 84 in a manner to reduce the volume of the reservoir 90 and to discharge the pharmaceutical composition stored within the reservoir 40 through fluid conducting passageways 96 of projecting structures 94 and into the body of the patient immediately below the stratum corneum. In this manner, the pharmaceutical composition is placed in contact with the lower epithelial layers and are able to be absorbed by the body.

Figure 5:
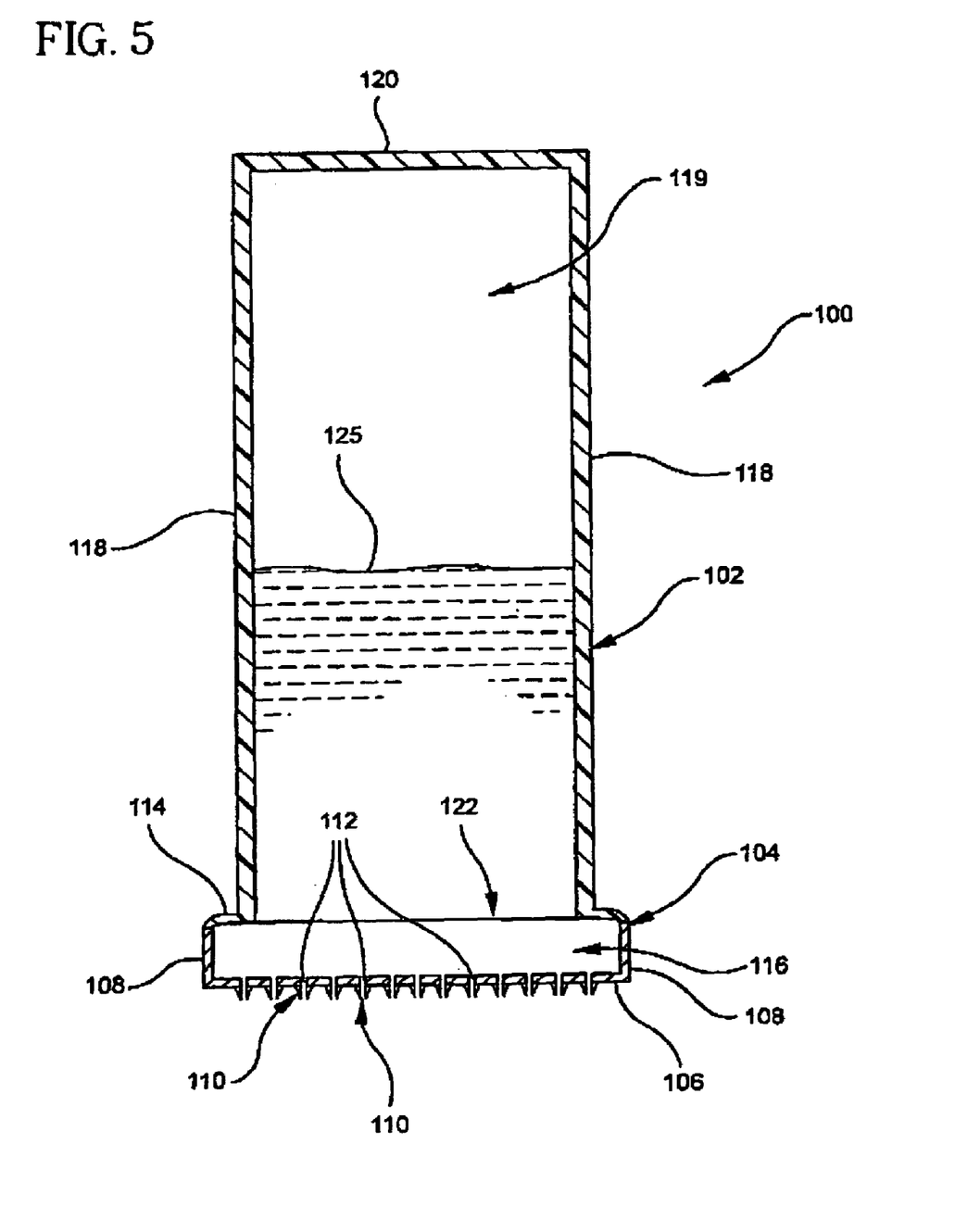
FIG. 5 is a cross-sectional side view of another embodiment of the present invention showing the side wall of the microdevice extended to a length such that its exterior surface defines a handle and the interior region created by the joining of the top wall and bottom wall of the microdevice defines a reservoir.
Figure 6:
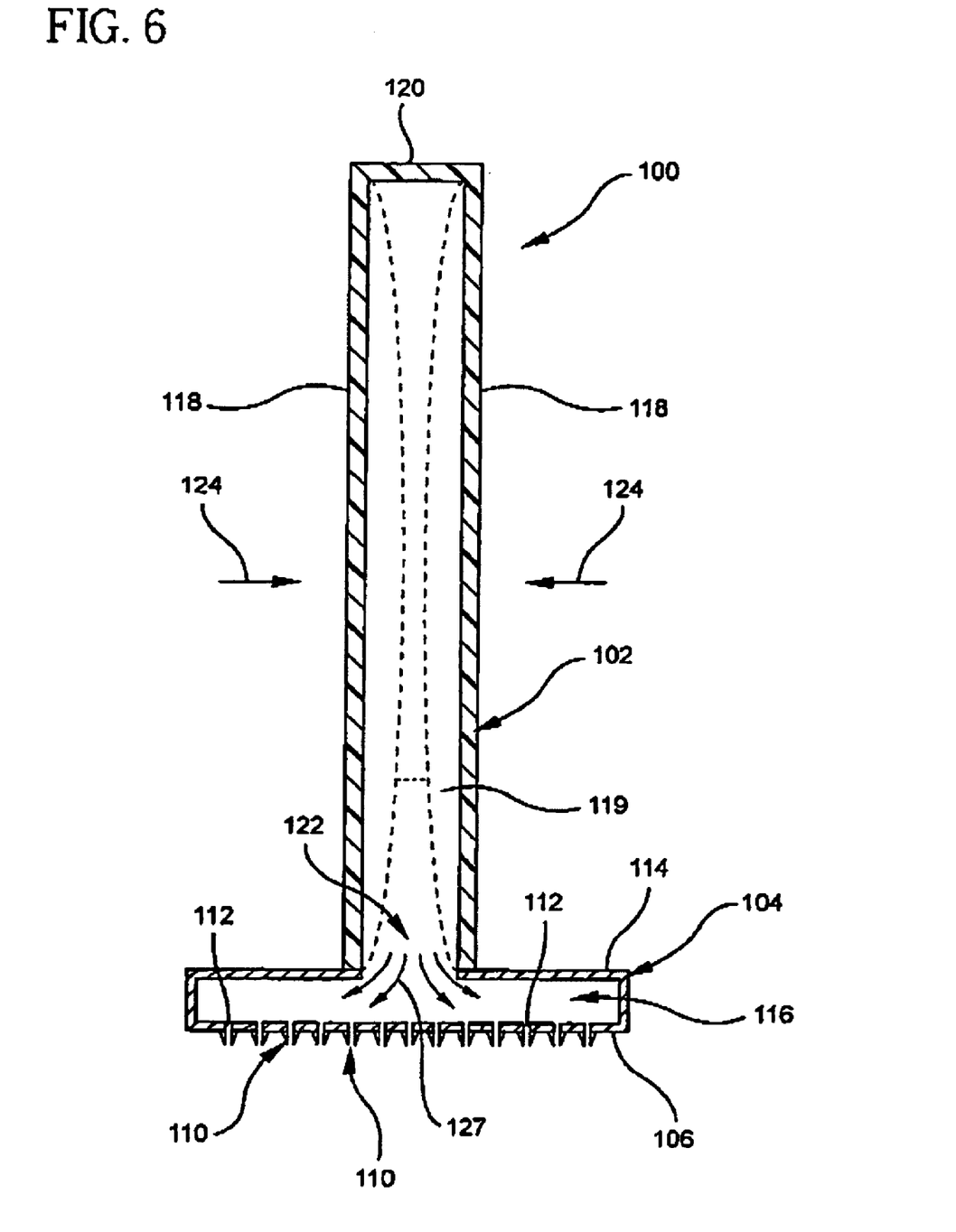
FIG. 6 is an end view in cross-section of the embodiment of FIG. 5.

EMBODIMENT OF FIGS. 5 AND 6

In another embodiment shown in FIGS. 5 and 6, a delivery device 100 includes a handle 102 attached to a base 104. Base 104 includes a bottom wall 106 and side walls 108. A plurality of projecting structures 110 arranged in an array extend from bottom wall 106. Projecting structures 110 in the embodiment illustrated, are microneedles having an axial passage 112 that extend through bottom wall 106. Base 104 also includes a top wall 114 coupled to side walls 108 to define a fluid reservoir 116.

Handle 102 is a hollow structure formed by side walls 118 and a top wall 120 to form an internal cavity 119. Handle 102 has an open bottom end 122 so that cavity 119 is in direct fluid communication with reservoir 116. As in the previous embodiment, handle 102 is made of a deformable resilient material so that side walls 118 can be deflected inwardly as shown by the phantom lines in FIG. 6 by applying an external force against the side walls 118 in the direction of arrows 124. In this embodiment, cavity 119 can contain a substance 125 to be delivered to the patient. Deflecting side walls 118 inwardly forces the substance 125 in the direction of arrows 127 from reservoir 116 through axial passages 112 of projecting structures 110.

Operation of the device 100 of this embodiment of the invention is substantially the same as the operation of the embodiment shown in FIG. 3, but offers an alternative configuration suitable for instances where a larger volume reservoir is desired.

Figure 7:
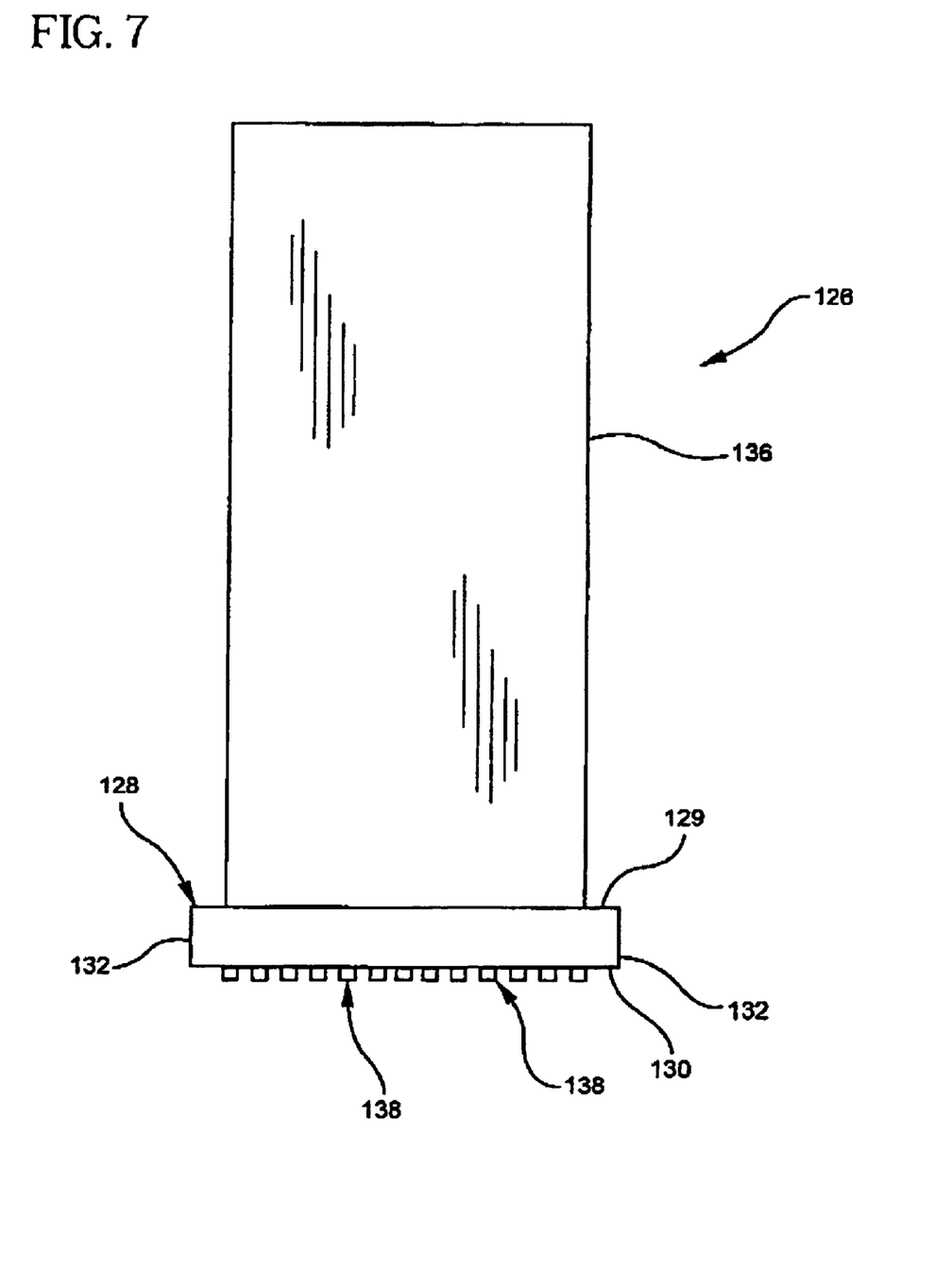
FIG. 7 is a front view of another embodiment of the present invention showing a handle coupled to a microdevice, where the microdevice includes a top wall and a bottom wall defining a reservoir.
Figure 8:
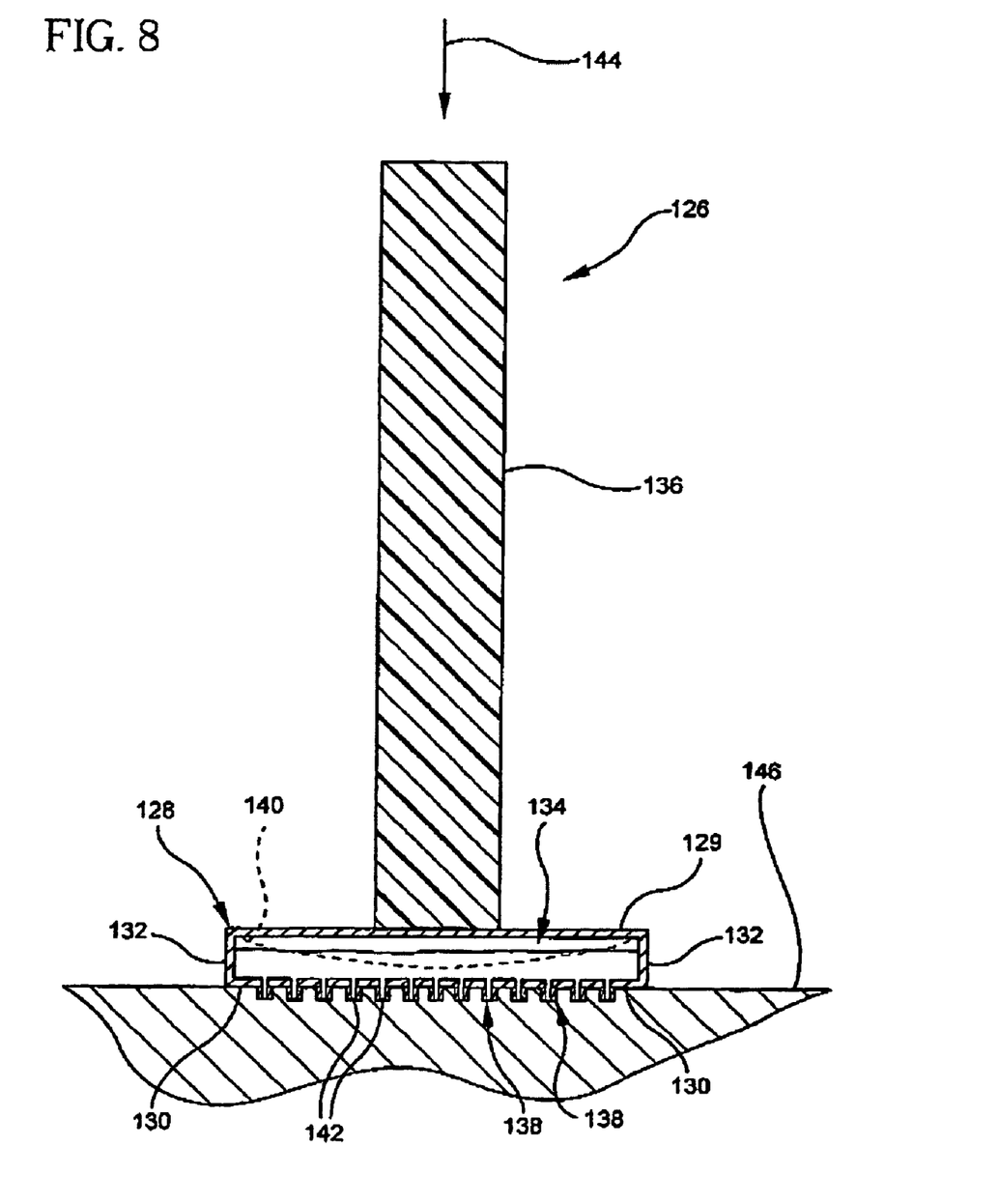
FIG. 8 is a cross-sectional side view of the embodiment of FIG. 7 showing a microdevice with a solid handle extending outwardly from the top wall of the microdevice.

FIGS. 7 and 8 show another embodiment of a delivery device 126 of the present invention including body 128 having a deformable top wall 129 spaced apart from a bottom wall 130 and side walls 132 extending between top wall 129 and bottom wall 130. The area enclosed by top wall 129, bottom wall 130 and side walls 132 define a reservoir 134. A solid manipulating member 136, such as a handle, is coupled to lop wall 129. In this embodiment, handle 136 is a solid, elongated member having a dimension to provide a surface which can be gripped by the user. By gripping handle 136, the person administering treatment can exercise accurate control over device 126 while minimizing the possibility of causing the patient undue irritation and discomfort. Bottom wall 130 has a plurality of outwardly extending projecting structures 142 having axial passages 138 communicating with reservoir 134. As in the previous embodiment, top wall 128 is sufficiently flexible to flex inwardly to dispense a substance 140 from reservoir 134 through axial passages 142 of projecting structures 142.

Once the device is positioned properly and projecting structures 142 are embedded within the stratum corneum, handle 136 can be pressed downwardly in the direction of arrow 144 to deflect top wall 129 as shown in phantom lines of FIG. 8. As in the previous embodiment, device 126 can be pressed downwardly against skin 146 to cause projecting structures 142 to penetrate skin 146 to a desired depth. Alternatively, device 126 can be rubbed against skin 146 in a target site to abrade skin 146 to a depth to allow substance 140 to penetrate skin 146 below the stratum corneum.

Once the device is positioned properly and projecting structures 138 are embedded within the stratum corneum, handle 136 can be pressed downwardly in the direction of arrow 144 to deflect top wall 129 as shown in phantom lines of FIG. 8. As in the previous embodiment, device 126 can be pressed downwardly against skin 146 to cause projecting structures 140 to penetrate skin 146 to a desired depth. Alternatively, device 126 can be rubbed against skin 146 in a target site to abrade skin 146 to a depth to allow substance 140 to penetrate skin 146 below the stratum corneum.

In other embodiments of the invention, the substance to be delivered is physically retained within the reservoir, such as for example, by at least one rupturable membrane. This retaining membrane may be as simple as a rupturable material overlaying, or adjacent to the fluid passageway or passageways, or an enclosing bladder. Other ways of retaining the substance are also within the scope and spirit of this invention. It is also envisioned that the membrane be ruptured by internally projecting members that will pierce the membrane. Regardless of the configuration of this retaining means the material or structure used needs to be responsive to the pressure generated by the dispensing means such that at a sufficient, and generally predetermine threshold, the pressure overcomes the ability of the retaining mean to retain the substance and the substance is dispensed.

While several embodiments have been chosen to illustrate the invention, it will be appreciated by those skilled in the art that various changes and modifications of the device can be made without departing from the scope of the invention as defined in the appended claims.

What is claimed is:

1. A device for administering a substance to a mammal, said device comprising:
    a top wall;
    a bottom wall spaced apart from said top wall and having a substantially planar outer surface;
    a plurality of projecting structures extending outwardly from said substantially planar surface from about 10 microns to about 1.5 mm;
    side walls joining said top wall and said bottom wall, said top wall, bottom wall and side walls defining a reservoir for said substance to be delivered;
    a device manipulating member which is deformable attached to at least one wall selected from said side walls, said top wall and combinations thereof and extending outward therefrom, said manipulating member having a dimension sufficient to grip and control said device; and at least one passageway in fluid communication with said reservoir, wherein said at least one wall is deformable.

2. The device of claim 1, wherein said manipulating member is defined by the exterior region of said side walls with said top wall defining an end of said manipulating member.

3. The device of claim 1, wherein said at least one passageway passes through each of said projecting structures.

4. The device of claim 1, wherein said projecting structures are substantially solid and said at least one passageway is in fluid communication with said substantially planar surface.

5. The device of claim 4, wherein said at least one passageway is in fluid communication with said projecting structures.

6. The device of claim 1, wherein said projecting structures have a length of from about 100 microns to about 250 microns.

7. The device of claim 1, wherein said projecting structures comprise an array of needle structures.

8. The device of claim 1, wherein said projecting structures comprise an array of structures having a length sufficient for penetrating only the stratum corneum by abrading.

9. The device of claim 1, wherein said reservoir contains a pharmaceutical composition.

10. The device of claim 1, wherein said manipulating member is hollow and defines a substantially sealed chamber, wherein said top wall is deformable whereby deforming said manipulating member applies a pressure against said top wall to deform said top wall and thereby dispense a substance from said reservoir.

11. A method of delivering a substance to a mammal comprising the steps of:
    placing the device for administering a substance of claim 1 in contact with the skin of the mammal;
    applying sufficient force to said device to cause said projecting structures of said device to penetrate the stratum corneum layer of said skin; and
    applying sufficient internal pressure to said substance in said reservoir of the device thereby dispensing said substance from said reservoir to said projecting structures and delivering said substance below the stratum corneum layer of the skin, wherein said internal pressure is generated by deforming a portion of said device wherein said portion is selected from said at least one wall, said manipulating member and combinations thereof.

12. The method of claim 11, wherein said projections comprise an array of microneedles having an axial passage in communication with said reservoir.

13. The method of claim 11, wherein said projections have a length of from about 80 to about 250 microns.

14. The method of claim 11, wherein said method further comprises moving said device whereby said projecting structures abrade said skin and penetrate into said stratum corneum.

15. The method of claim 11, wherein said manipulating member is a handle having a dimension to grip said device.

16. The method of claim 11, wherein said top wall is made of a flexible material and said projecting structures are hollow members having an axial passage in communication with said reservoir, said method comprising applying a downward pressure on said top wall to deflect said top wall into said reservoir and to dispense said substance from said reservoir.

17. A device for administering a substance to a mammal, said device comprising:
   a top wall;
   a bottom wall spaced apart from said top wall and having a substantially planar outer surface;
   a plurality of projecting structures extending a pre-selected distance outwardly from said substantially planar surface from about 10 microns to about 1.5 mm;
   side walls joining said top wall and said bottom wall, said top wall, bottom wall and side walls defining a fluid conduit, said fluid conduit in fluid communication with said projecting structures;
   a device manipulating member attached to said top wall and extending outwardly therefrom, said manipulating member having a dimension sufficient to grip and control said device; said manipulating member having a deformable portion; said manipulating member housing a reservoir and at least one passageway in selectable fluid communication with said fluid conduit, wherein selective fluid communication said reservoirs and said fluid conduit allows said substance to communicate with said projecting structures via said fluid conduit.

18. The device of claim 17, wherein selectable fluid communication is enabled by a pre-selected pressure applied to said reservoir by deformation of a portion of said manipulating member, thereby dispensing said substance from said reservoir to said fluid conduit.

19. The device of claim 17, wherein said manipulating member is defined by the exterior region of said side walls with said top wall defining an end of said manipulating member.

20. The device of claim 17, wherein said at least one passageway passes through each of said projecting structures.

21. The device of claim 17, wherein said projecting structures are substantially solid and said at least one passageway is in fluid communication with said substantially planar surface.

22. The device of claim 21, wherein said at least one passageway is in fluid communication with said projecting structures.

23. The device of claim 17, wherein said projecting structures have a length of from about 100 microns to about 250 microns.

24. The device of claim 17, wherein said projecting structures comprise an array of needle structures.

25. The device of claim 17, wherein said projecting structures comprise an array of structures having a length sufficient for penetrating only the stratum corneum by abrading.

26. The device of claim 17, wherein said reservoir contains a pharmaceutical composition.

27. The device of claim 17, wherein said manipulating member is hollow and defines a substantially sealed chamber, wherein said top wall is deformable whereby deforming said manipulating member applies a pressure against said top wall to deform said top wall and thereby dispense a substance from said reservoir.

* * * * *